(12) United States Patent
Jang et al.

(10) Patent No.: US 7,250,422 B2
(45) Date of Patent: Jul. 31, 2007

(54) PHARMACEUTICAL COMPOSITION CONTAINING BERBERINE AS EFFECTIVE INGREDIENT FOR PREVENTING AND TREATING ADDICTION OR TOLERANCE TO MORPHINE

(75) Inventors: Choon-Gon Jang, Gyeonggi-do (KR); Seok-Yong Lee, Seoul (KR)

(73) Assignee: Sungkyunkwan University, Seoul (KR)

( * ) Notice: Subject to any disclaimer, the term of this patent is extended or adjusted under 35 U.S.C. 154(b) by 0 days.

(21) Appl. No.: 10/532,196

(22) PCT Filed: Oct. 27, 2003

(86) PCT No.: PCT/KR03/02280

§ 371 (c)(1),
(2), (4) Date: Apr. 21, 2005

(87) PCT Pub. No.: WO2004/039372

PCT Pub. Date: May 13, 2004

(65) Prior Publication Data

US 2006/0035917 A1    Feb. 16, 2006

(30) Foreign Application Priority Data

Oct. 29, 2002  (KR) .................. 10-2002-0066029
Aug. 29, 2003  (KR) .................. 10-2003-0060353

(51) Int. Cl.
*A61K 31/4745* (2006.01)
(52) U.S. Cl. ................................... 514/283
(58) Field of Classification Search ............. 514/283
See application file for complete search history.

(56) References Cited

U.S. PATENT DOCUMENTS 6,692,777 B2 *  2/2004  Lee ........................... 424/725

FOREIGN PATENT DOCUMENTS

| KR | 1999-0036248 | 5/1999 |
| KR | 10-0277481 | 10/2000 |
| KR | 10-0281003 | 11/2000 |

OTHER PUBLICATIONS

A. Brissemoret, 'Note sur Less Plantes Anti-Opium', Comptes Rendus des Seances de la Societe de Biologie et de Ses Filiales, 1925, vol. 93, 1341-1343 p. 1342, paragraph 6-7; claim 1-4.
Anna Capasso, Nunziatina de Tommasi, Luca Rastrelli, Francesco de Simone, 'New Protopine Alkaloids from Aristolochia constrieta Reduce Morphine Withdrawl in vitro', Phytother. Res., 2000, vol. 14, 653-655 the whole document ;claim 1-4.
Ge Xiaoqun, Zhang Hongquan, Zhou Hauzhu, Xu Shengxin, Bian Chunfu, 'Experimental Study of Tetrahyrdoprotoberberines Inhibiting Morphine Withdrawl Syndromes', Chin. J. Drug Depend., 1999, vol. 8, No. 3, 195-198 the whole document, claim 1-4.
Jin Gz, Wang Xl, Shi Wx, 'Tetrahydroprotoberberine-a New Chemical Type of Antagonist of Dopamine Receptors', Sie Sin B, 1986, vol. 29+ No. 5, 527-534 the whole document; claim 1-4.

* cited by examiner

*Primary Examiner*—Kamal A. Saeed
*Assistant Examiner*—Yong Chu
(74) *Attorney, Agent, or Firm*—Jordan and Hamburg LLP

(57) ABSTRACT

Disclosed is a pharmaceutical composition for preventing and treating addiction to morphine or preventing and inhibiting the development of tolerance to the analgesic effects of morphine, containing berberine as an effective ingredient, wherein the berberine has an inhibitory effect versus psychological dependence on abused drugs such as morphine and the increase of spontaneous locomotor activity upon administration of the drugs, The pharmaceutical composition and a *Coptis japonica* plant extract of the present invention, which contain berberine, are highly effective in inhibiting the aforementioned symptoms of morphine addiction, and are thus useful for prevention and treatment of addiction to abused drugs such as morphine. In addition, the pharmaceutical composition additionally containing a pharmaceutical acceptable carrier can be applied to prevent and inhibit morphine tolerance caused by repeated administration of morphine, while not affecting the analgesic effects of morphine upon a single administration.

2 Claims, 4 Drawing Sheets

PHARMACEUTICAL COMPOSITION CONTAINING BERBERINE AS EFFECTIVE INGREDIENT FOR PREVENTING AND TREATING ADDICTION OR TOLERANCE TO MORPHINE

TECHNICAL FIELD

The present invention, in general, relates to a pharmaceutical composition for preventing and treating the harmful actions of narcotic analgesic agents. More particularly, the present invention relates to a pharmaceutical composition comprising berberine as an effective ingredient, where the composition has inhibitory effects versus psychological dependence on morphine and an increase of spontaneous locomotor activity induced by morphine.

People who abuse drugs typically suffers from psychological dependence which is a compulsion for the continuous administration of a drug for its euphoric effects despite any adverse effects that may occur, and include morphine or derivatives thereof, cocaine, and methamphetamine or derivatives thereof.

Morphine, which is a narcotic analgesic agent, has the psychological excitatory effects with most common symptoms of hallucinosis and delirium when used in relatively high doses or when repeatedly used for longer periods even in low doses. Such psychotoxicity occurrence is augmented by the repeated administration of morphine, and a very high physical and psychological dependence is thus developed. That is, the abused drugs have the major properties of exciting the central nervous system and increasing the psychological craving for continuous consumption of the drugs. The abused drugs increase spontaneous locomotor activity by continuous administration and induce psychological dependence thereon.

The continuous administration of the abused drugs leads to the exhaustion of dopamine and reduced activity of dopamine in the nervous system. To compensate for the reduced activity of dopamine, dopamine neurons are activated. Thus, the postsynaptic dopamine receptors become hypersensitive, and spontaneous locomotor activity is increased, resulting in the development of strong craving for the continuous consumption of the drugs. Due to such a psychoactive effect of morphine, users depending on morphine have been continuously increased. Since such abuse of morphine causes severe social problems, there is an urgent need for the development of agents for treating and preventing morphine addiction.

PRIOR ART

Korean Pat. No. 10-0277481 discloses isatinoxime derivatives, which serve as antagonists versus neurotoxic effects of excitatory amino acids and thus are useful for treatment of excitatory amino acid-dependent diseases in the central nervous system, cerebrovascular diseases, mental illness, etc. However, currently, there is no development for drugs with obvious therapeutic and preventory efficacies on an increase of spontaneous locomotor activity and psychological dependence, which are caused by the abused drugs such as morphine. Thus, the abused drugs are problematic in terms of having harmful side effects such as the increase of spontaneous locomotor activity and the development of psychological dependence. In particular, the abuse and addiction of the drugs have led to severe social problems.

On the other hand, analgesic agents are medical drugs that are typically used for inhibiting or alleviating acute pains. The analgesic agents are typically classified into narcotic and non-narcotic types. The narcotic analgesic agents have been clinically used for treating acute pains in late-stage cancer patients due to their excellent analgesic effect versus visceral pains. However, as described above, when the narcotic analgesic agents are administered in relatively high doses or repeatedly administered for longer periods even in low doses, the habitual administration of the analgesics and the craving for the analgesic agents can be developed. Also, when a user is repeatedly exposed to a narcotic analgesic agent of a predetermined amount, tolerance to the analgesic agent is rapidly developed, resulting in the reduction of the analgesic effect of the analgesic. Thus, the narcotic analgesic agent should be used in an increased dose in order to obtain a desired analgesic effect. Such an increased dose of the narcotic analgesic agent causes different side effects and, thus, is severely toxic to humans.

As a representative example of the narcotic analgesic agent, morphine is know to have the highest analgesic effect among analgesics developed to date. However, the repeated administration of morphine causes gradual reduction in its analgesic effect and finally the development of tolerance to the analgesic effect of morphine. For these reasons, morphine is limited in its application to the clinical fields despite its excellent efficacy. Therefore, in order to utilize morphine as an analgesic agent, it is very important that the morphine's initial analgesic effect is maintained without reduction in the analgesic effect upon repeated administration. This purpose can be achieved by inhibiting the development of tolerance to morphine.

A pharmaceutical composition for preventing or inhibiting the development of tolerance to the analgesic effect of the narcotic analgesics such as morphine is described in Korean Pat. Publication No. 1999-0036248 (Application No. 10-1998-0700916), which discloses a pharmaceutical composition with an inhibitory effect versus the development of psychological dependence and/or tolerance for narcotic analgesics, comprising 2-(1-pyrrolidinyl)acetateamide derivatives as effective ingredients. However, with respect to components of compositions, the above pharmaceutical composition differs from the present pharmaceutical composition comprising berberine. Also, a pharmaceutical composition containing berberine is disclosed in Korean Pat. No. 10-0281003, which, in detail, comprises protoberberine alkaloid compounds as effective ingredients and has an anti-depressing effect. However, this composition that may be used as anti-depressant differs from the present pharmaceutical composition having an inhibitory effect versus morphine tolerance by the action of berberine.

DISCLOSURE OF THE INVENTION

Leading to the present invention, the intensive and thorough research onto to develop preventory or therapeutic agents for addiction to the abused drugs, conducted by the present inventors, resulted in the finding that naturally occurring berberine, a major component of *Coptis japonica* and *Phellodendron amurense* plants, has a significant inhibitory effect versus psychological dependence in an animal model with induced psychological dependence.

It is therefore an object of the present invention to provide a pharmaceutical composition for preventing and treating morphine addiction.

Also, the present inventors attempted to develop pharmaceutical preparations having an inhibitory effect versus the morphine tolerance caused by repeated administration of morphine. This research resulted in the finding that naturally occurring berberine, a major component of *Coptis japonica*, *Phellodendron amurense* and *Berberis koreana* plants, has a strong inhibitory effect versus morphine tolerance.

Therefore, it is another object of the present invention to provide a pharmaceutical composition for preventing and inhibiting the development of morphine tolerance, comprising berberine as an effective ingredient.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE INVENTION

Figure 1:
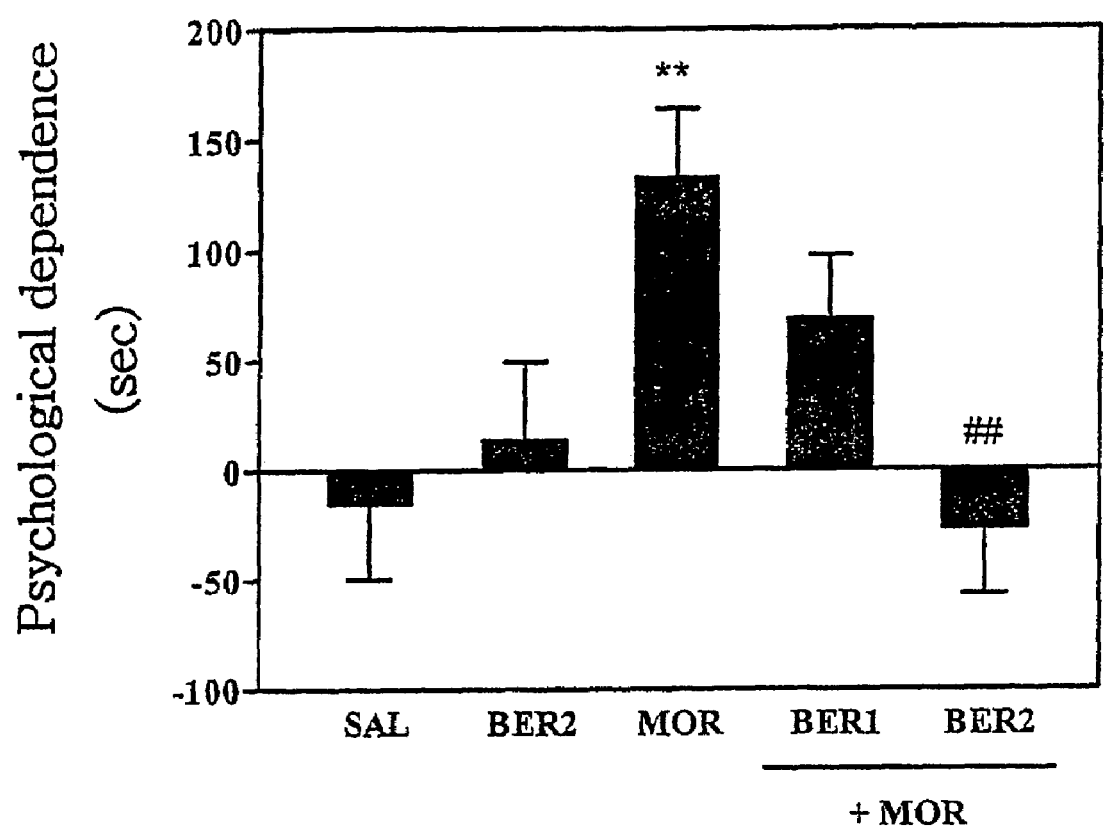
FIG. 1 is a graph showing an inhibitory effect of berberine versus psychological dependence caused by berberine in mice.

The meaning of the abbreviations on the drawings are as follows:

| | |
|---|---|
| sec = | second |
| SAL = | saline |
| BER = | berberine |
| MOR = | morphine |
| AUC = | area under the curve |
| DW = | distilled water |

The present invention provides a novel use of berberine and a pharmaceutical composition comprising berberine. More particularly, the present invention provides a pharmaceutical composition for preventing and treating morphine addiction or preventing and inhibiting the development of tolerance to the analgesic effect of morphine, comprising berberine as an effective ingredient.

In an aspect of the present invention, there is provided a pharmaceutical composition for preventing and inhibiting morphine addiction and the development of tolerance to the analgesic effect of morphine, comprising a pharmaceutically acceptable carrier along with the above effective ingredient.

In another aspect of the present invention, there is provided a use of berberine for preparation of a pharmaceutical composition for preventing and inhibiting morphine addiction and the development of tolerance to the analgesic effect of morphine.

In the pharmaceutical composition of the present invention, the effective ingredient berberine (7,8,13,13a-tetradihydro-9,10-dimethoxy-2,3-(methyldioxy)berbinium), belonging to the isoquinolineakaloid family, can be extracted from a variety of plants, for example, from the root of Coptis japonica and the bark of *Phellodendron amurense*, where the two plants belong to the family *Berberidaceae*. The berberine was used for staining wool, silk, leather, and the like. The berberine, currently used for medical purposes, is known to have antibacterial, intestine-regulating and anti-ulcer effects. Safe doses of the berberine are described in the literature, and the berberine is known to have a LD50 value of 90 mg/kg (intraperitoneal injection) in rats (see, Tang, W. and Eisenbrand, G., Chinese Drugs of Plant Origin, pp. 362-371, Springer Verlag, Berlin, Heidelberg, N.Y.). The berberine used in the pharmaceutical composition of the present invention is commercially available.

The daily dosage of the berberine used as an effective ingredient in the present pharmaceutical composition may be determined depending on patient's age, body weight and pathological states, and typically ranges from 20 to 100 mg (intraperitoneal injection) or 50 to 400 mg (oral administration). Also, the dosage of the berberine may be properly determined by experience of those skilled in the art. The berberine is currently used as a medical drug, and known to rarely have toxicity when administered to the body in the typical doses. Therefore, it will be understood by those of ordinary skills in the art that the pharmaceutical composition for preventing and inhibiting morphine addiction and the development of tolerance to the analgesic effect of morphine, comprising an effective amount of berberine, is safe because of not having harmful side effects to the humans.

In the present invention, a narcotic analgesic agent is exemplified by only morphine in the above part of this specification. However, if tolerance to the narcotic analgesic agent is induced by single administration or repeated administration for short or long periods, the narcotic analgesic agent is not limited to morphine. Non-limiting examples of the narcotic analgesic include morphine derived from opium and its semi-synthetic derivatives, and non-natural compounds having the morphine-like effect, such as pethidine, and salts thereof. In more detail, the narcotic analgesic agent is exemplified by alkaloids derived from opium and their semi-synthetic derivatives such as phenanthrenes (e.g., morphine, oxymorphone, hydromorphone, codeine, hydrocodone, heroin, thebaine and buprenorphine); phenylpiperidines (e.g., meperidine and fentanyl); phenylheptylamine (e.g., methadone and propoxylphene); morphinans (e.g.; levolphanol, methorphan and levolphan); and benzomorphans (e.g., phenazocine and pentazocine).

The present pharmaceutical composition comprising berberine, according to its formulation, may further comprise a pharmaceutically acceptable carrier commonly used in the art. In detail, the present pharmaceutical composition comprising berberine may be administered in the form of oral preparations or injection preparations. Examples of the oral preparations may include tablets and gelatin capsules. The oral preparations, in addition to the active ingredient, may comprise a diluent (e.g., lactose, dextrose, sucrose, mannitol, sorbitol, cellulose and/or glycine), and a lubricant (e.g., silica, talc, stearic acid and magnesium or calcium salts thereof and/or polyethylene glycol). Preferably, the tablets may further comprise a binder (e.g., magnesium aluminum silicate, starch paste, gelatin, tragacanth, methylcellulose, sodium carboxymethylcellulose and/or polyvinylpyrrolidine), and, if desired, may further comprise a disintegrator (e.g., starch, agar, arginic acid or sodium salts thereof, or a mixture thereof), and/or an absorbent, a colorant, a flavoring agent and a sweetening agent. The injection preparations may be preferably an isotonic solution or a suspension, and may be sterilized or comprise an adjuvant (e.g., an antiseptic, a stabilizer, a wetting agent or an emulsifier, a salt for osmotic regulation and/or a buffering agent). In addition, the formulations may further comprise other therapeutically useful substances.

The berberine as an effective ingredient of the pharmaceutical composition of the present invention was found not to affect the analgesic effect of morphine upon a single administration. In addition, the berberine was found to have an effect of significantly inhibiting the development of tolerance to the analgesic effect of morphine induced by repeated administration while maintaining the initial analgesic effect of morphine. Therefore, the pharmaceutical composition of the present invention may be used to prevent the development of tolerance to the analgesic effect of morphine upon administration with morphine. Consequently, the present pharmaceutical composition may be used with a purpose for preventing the development of morphine tolerance. In addition, the present pharmaceutical composition has an effect of inhibiting and alleviating tolerance to the analgesic effect of morphine, induced by repeated administration with morphine. Thus, the present pharmaceutical composition may be therapeutically used with an aim to inhibit the previously induced tolerance to morphine, along with morphine administration.

The present invention will be explained in more detail with reference to the following examples in conjunction with the accompanying drawings. However, the following examples are provided only to illustrate the present invention, and the present invention is not limited to the examples.

EXAMPLES

Method and Materials

Male ICR mice weighing 18 to 25 g were adapted to a new environment by being grown for over one week in a breeding room under a controlled temperature and humidity. 10 to 15 mice per group were used. Morphine and berberine were purchased from the Keukdong Pharm Company (Inchon, Korea) and the Sigma Company (USA), respectively.

Example 1

Evaluation of Inhibitory Effect of Berberine Versus the Development of Psychological Dependence for Morphine The development of psychological dependence on morphine was detected by the conditioned place preference test.

Conditioned place preference was performed in two boxes of equal size (15×15×15 cm) were used, each which has a forehead surface made of a transparent acrylic plate. The remaining three surfaces of each box were made of a white or black acrylic plate. The two boxes were connected with a gray passage (3×3×7.5 cm), and the passage could be blocked with a removable gillotine door. To allow the mice to feel the texture of the floor of the boxes, the white box had a tough floor, and the black box had a smooth floor. The mice were grown under a light intensity of 20 Lux.

Step 1 (Preconditioning Phase)

On day 1, the guillotine door of the boxes was open, and the mice were allowed to explore both compartments freely for 5 min. On day 2, the mice were placed in the boxes in the same way as in day 1, and the times spent in both boxes were measured for 15 min and used as control latency.

Step 2 (Conditioning Phase)

On days 3, 5, 7 and 9, the guillotine door was closed. The mice were intraperitoneally administered with 5 mg/kg of morphine, and placed for one hour in the white box with the hatred effect. On days 4, 6, 8 and 10, the mice were administered with physiological saline and placed for one hour in the black box with the preference effect. One hour before the morphine administration, 1 or 2 mg/kg of berberine was orally administered to the mice.

Step 3 (Testing Phase)

On day 9, after the guillotine door was opened, the times the mice spent in the boxes were measured for 15 min, wherein the mice were not administered with any drug, and compared to those measured on day 2. The degree of the development of psychological dependence was calculated by subtracting the preconditioning time from the testing time. As shown in FIG. 1, a morphine control showed a significant psychological dependence (p<0.01). In contrast, in the mice administered with morphine and berberine, the psychological dependence was completely inhibited (p<0.01) to the level equal to the control treated with physiological saline. These results indicate that berberine has an excellent inhibitory effect versus psychological dependence on morphine.

Example 2

Figure 2:
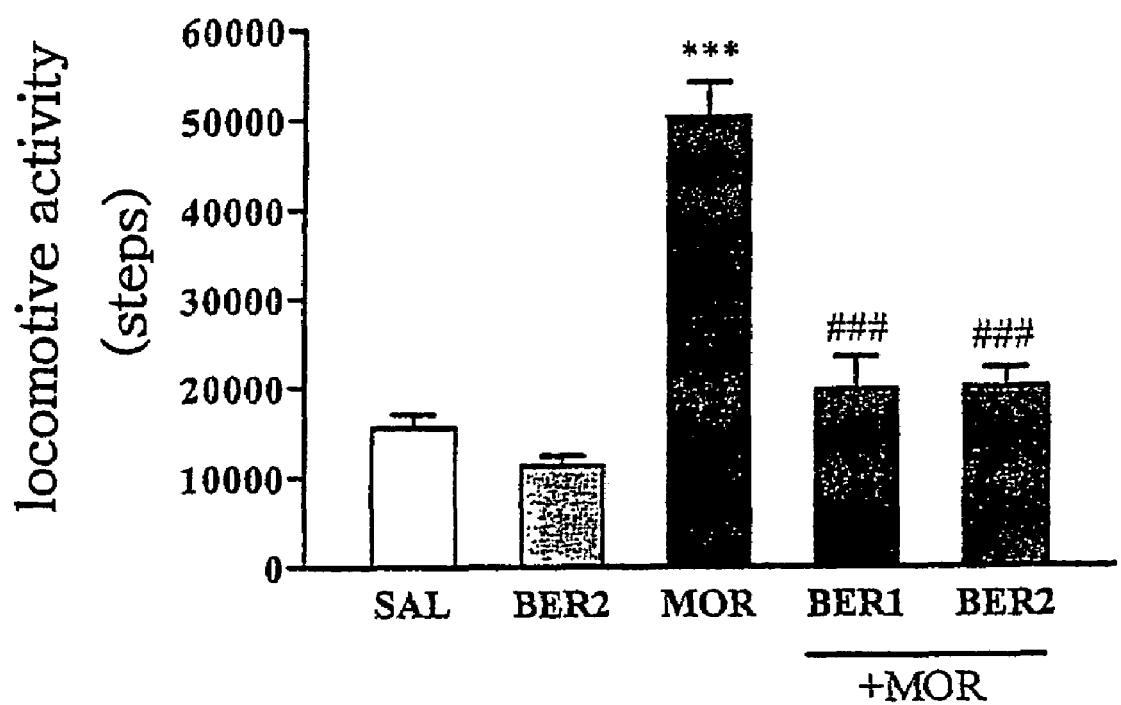
FIG. 2 is a graph showing an inhibitory effect of berberine versus spontaneous locomotor activity increased by berberine in mice.

Evaluation of Inhibitory Effect of Berberine Versus Increase of Spontaneous Locomotor Activity by Morphine Spontaneous locomotor activity was tested in a plastic chamber (26×30×30 cm) using a Video-tracking system. First, the mice were administered with 10 mg/kg of morphine once per day for six days. Immediately after the last administration, the mice were placed in the plastic chamber, and spontaneous locomotor activity was recorded for 30 min and analyzed using a computer program. Berberine was orally administered to the mice in amounts of 1 and 2 mg/kg one, hour before administration of morphine. The results are given in FIG. 2. As shown in FIG. 2, when administered with only morphine, the mice showed a remarkably increased locomotor activity of 50242 steps by a forefoot. In contrast, when pre-administered with 1 and 2 mg/kg of berberine, the mice displayed locomotor activities of 19744 steps and 20027 steps. That is, berberine was found to significantly suppress the locomotor activity increased by morphine by 61% and 60% (p<0.001, respectively) in comparison with the morphine control group.

Example 3

Evaluation of the Effects of Berberine on the Analgesic Effect of Morphine Upon a Single Administration Male ICR mice weighing 18 to 25 g were adapted to a new environment by being grown for over one week in a breeding room under controlled temperature and humidity. 10 mice per group were used. Morphine and berberine (berberine hemisulfate) were purchased from the Keukdong Pharm Company (Inchon, Korea) and the Sigma Company (USA), respectively, and dissolved in distilled water before use.

The effect of berberine on the analgesic action of morphine was assessed by a hot-plate test applying a heat stimulus to mice. For the hot-plate test, each mouse was placed on a hot plate at 52° C. and the latency until mouse showed first signs of discomfort (hind paw-licking or jumping) was observed. To avoid tissue damage, an artificial maximum time for exposure to heat was imposed (cut-off time), which was 30 sec. In case of not showing the behavioral response for over 30 sec, mice were taken off the hot plate. The mice were intraperitoneally administered with distilled water and berberine of 1, 3 and 10 mg/kg. After 30 min, the mice were subcutaneously injected with distilled water and morphine of 5 mg/kg. 30, 60 and 90 min after the injection, licking or jumping responses of the mice to heat from the hot plate was measured according to the same method as in the recording of the latency, with a maximum time of 30 sec. The results are expressed as "percentage maximal possible effect (% MPE)", which was calculated according to an equation, below, and the strength of the analgesic action of morphine was expressed as "Area Under the Curve (AUC)".

$$MPE\ (\%) = (Tt-To)/(Tc-To) \times 100$$

wherein, Tc is the cut-off time, Tt is the test latency, and To is the control latency.

Figure 3:
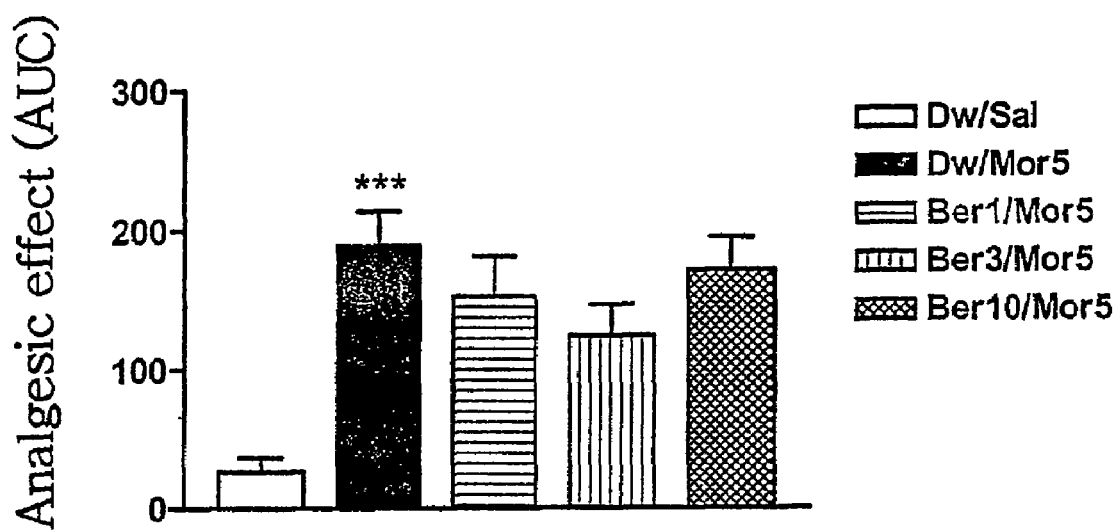
FIG. 3 is a graph showing an effect of berberine on the analgesic effect of morphine when morphine was administered once to mice.

As shown in FIG. 3 (significant difference between control and morphine-treated group: ***$P<0.001$), the morphine-treated group showed a significantly increased analgesic effect, compared to the control group treated with physiological saline. In addition, in the groups pre-treated with berberine of 1, 3 and 10 mg/kg, berberine was found to rarely affect the analgesic effect of morphine.

Example 4

Evaluation of Effects of Berberine Versus the Development of Morphine Tolerance Caused by Repeated Administration Berberine was evaluated for an effect on the development of morphine tolerance by repeated administration. Mice were pretreated with distilled water and berberine of 1, 3 and 10 mg/kg by intraperitoneal injections. After 30 min, the mice were subcutaneously injected with physiological saline and morphine of 10 mg/kg once per day for six days. The next day, that is, on day 7, behavioral responses of the mice to heat on a hot plate were observed according to the same hot-plate test as in the Example 3. The development of tolerance to the analgesic effect of morphine was expressed as AUC, which was calculated according to the same method as in the Example 3.

Figure 4:
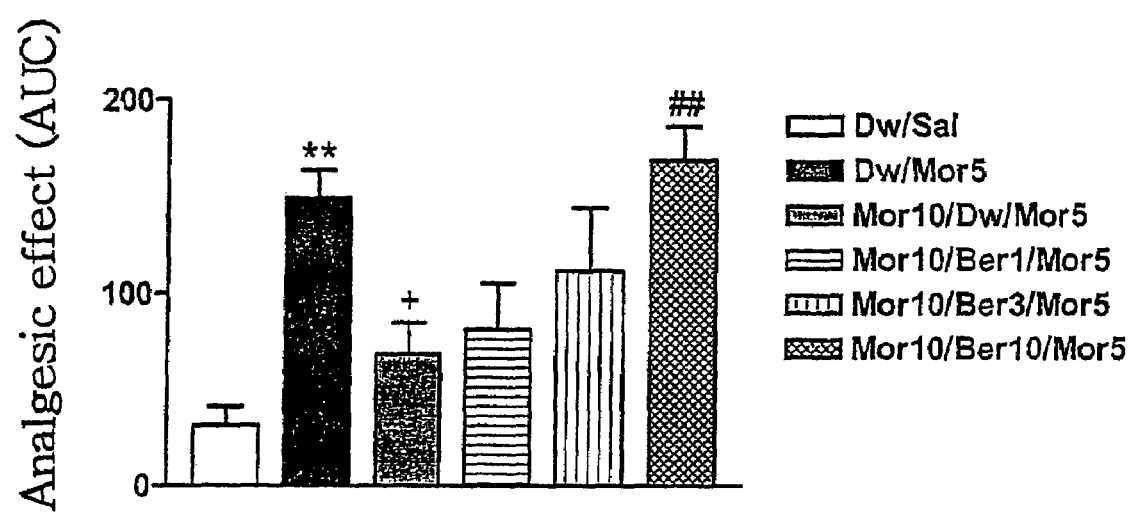
FIG. 4 is a graph showing an inhibitory effect of berberine versus tolerance to the analgesic effect of morphine when morphine was repeatedly administered to mice.

As shown in FIG. 4 (significant difference between control and morphine-treated group with a single administration: ***$P<0.01$; significant difference between control and morphine-treated group with morphine tolerance: $^+P<0.05$; significant difference between group with morphine tolerance and berberine-treated group: $^{++}P<0.01$), when mice were repeatedly administered with morphine, the initial analgesic effect of morphine was greatly reduced, indicating that morphine tolerance was developed. In contrast, in the group pretreated with berberine of 10 mg/kg, such morphine tolerance was found to be significantly inhibited.

INDUSTRIAL APPLICABILITY

As described hereinbefore, berberine nearly completely recovered the morphine-poisoned mice to the level of normal mice (physiological saline-treated group), indicating that berberine has an effect of greatly alleviating addiction to morphine. In addition, berberine significantly inhibited the increase of spontaneous locomotor activity by repeated administrations of morphine. Therefore, berberine is useful for the prevention and treatment of morphine addiction.

In addition, the pharmaceutical composition of the present invention has the excellent effects on prevention and inhibition of the development of tolerance to the analgesic effect of morphine upon repeated administration, while not affecting the analgesic effect of morphine upon a single administration. Therefore, the present composition is very useful for preventing or alleviating the development of tolerance to morphine.

The inevntion claimed is:

1. A method for inhibiting a person from development of tolerance to analgesic effects of morphine comprising administering to such person a pharmaceutical composition having berberine as an effective ingredient.

2. A method according to claim 1, wherein the pharmaceutical composition comprises a pharmaceutically acceptable carrier.

* * * * *